United States Patent
Gabel et al.

(10) Patent No.: US 6,521,262 B2
(45) Date of Patent: *Feb. 18, 2003

(54) SOLID INSTANT-RELEASE FORMS OF ADMINISTRATION AND PROCESS FOR PRODUCING THE SAME

(75) Inventors: Rolf-Dieter Gabel, Schwetzingen (DE); Alexander Wirl, Heuchelheim (DE); Heinrich Woog, Laudenbach (DE)

(73) Assignee: Heidelberg Pharma Holding GmbH, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,170
(22) PCT Filed: Jan. 24, 1997
(86) PCT No.: PCT/EP97/00329
§ 371 (c)(1),
(2), (4) Date: Jul. 27, 1998
(87) PCT Pub. No.: WO97/26867
PCT Pub. Date: Jul. 31, 1997

(65) Prior Publication Data
US 2002/0122817 A1 Sep. 5, 2002

(30) Foreign Application Priority Data
Jan. 26, 1996 (DE) .......................... 196 02 757

(51) Int. Cl.$^7$ .................................. A61K 9/14
(52) U.S. Cl. ...................... 424/498; 424/489
(58) Field of Search ................ 424/400, 450, 424/489–502

(56) References Cited

U.S. PATENT DOCUMENTS

| | | | |
|---|---|---|---|
| 4,164,560 A | | 8/1979 | Folkman et al. |
| 4,283,394 A | * | 8/1981 | West .......................... 424/182 |
| 4,605,551 A | * | 8/1986 | Buehler ....................... 424/38 |
| 4,622,392 A | * | 11/1986 | Hong .......................... 536/29 |
| 4,999,189 A | | 3/1991 | Kogan et al. |
| 5,223,263 A | | 6/1993 | Hostetler et al. |

FOREIGN PATENT DOCUMENTS

| | | |
|---|---|---|
| WO | WO 92 03462 | 3/1992 |
| WO | WO 92 10172 | 6/1992 |

OTHER PUBLICATIONS

Hirai, et al., "Formulation studies of a new oral cephalosporin, cefotiam hexetil hydrochloride", Chemical Abstracts, vol. 110, No. 14, 1989, abstract.

Hirai, et al., Formulation studies of a new oral cephalosporin, cefotiam hexetil hydrochloride, Chemical Abstracts, vol. 48, No. 3, 1988, pp. 189–196.

* cited by examiner

Primary Examiner—Gollamudi S. Kishore
(74) Attorney, Agent, or Firm—Arent Fox Kintner Plotkin & Kahn, PLLC

(57) ABSTRACT

The present invention concerns solid instant-release forms of administration (IR form of administration) comprising therapeutic active substances or active substance concentrates in particular lipid conjugates of nucleosides which have gel-forming properties in aqueous media as well as processes for their production.

47 Claims, 1 Drawing Sheet

EMBEDDING THE ACTIVE SUBSTANCE IN A PRIMARY AND SECONDARY ENVELOPE

SOLID INSTANT-RELEASE FORMS OF ADMINISTRATION AND PROCESS FOR PRODUCING THE SAME

The present invention concerns solid instant-release forms of administration (IR forms of administration) comprising therapeutic agents or concentrates of active substances in particular lipid conjugates of nucleosides which have gel-forming properties in aqueous media. The invention additionally concerns processes for the production of such instant-release forms.

Medicinal substances (active substances) are only used in the rarest cases without being made into a particular form. It is well-known that auxiliary substances can be used to convert them into solid IR forms of administration with conventional galenic processes.

As a rule IR forms of administration should disintegrate very rapidly in order to achieve the required high in vitro dissolution rates of the active substance. The rapid disintegration of the form of administration is determined on the one hand by the selection of the auxiliary substances and of the production process but on the other hand also by the dissolution properties of the active substance itself. The active substances used should usually not form gels or gel-like structures when they dissolve in aqueous media in order to exclude as far as possible a mutual agglutination of the individual particles of active substance.

However, there are also numerous active substances with a lipophilic residue e.g. active substances from the group of lipid conjugates which, when processed to form solid IR forms of administration using conventional galenic processes, tend to form gels or gel-like structures when they dissolve in aqueous media and thus adequately rapid in vitro dissolution rates of the active substance are not achieved. This also applies to blends of active substances which contain the active substance in a high concentration (concentrates of active substances). This disadvantage becomes particularly apparent when monolithic forms of administration (e.g. tablets) in high dosages are desired, the described effect increasing with increasing concentrations of active substance. The in vitro dissolution rate of these formulations and thus also the dissolution rate and resorption rates in vivo are greatly reduced compared to liquid forms of administration.

Within the sense of the invention the term gel-forming active substances is understood to include those active substances which form gel-like phases at concentrations of less than 20% (w/v %) in aqueous systems at 20° C. and the solutions resulting therefrom do not exhibit Newtonian flow behaviour. Those fluids are referred to as Newtonian fluids whose flow resistance at a given temperature defined by the Newtonian equation $t = h \cdot D$ is a material constant in which t is the shear stress, D denotes the velocity gradient and h denotes the dynamic viscosity.

Such active substances and the production thereof are described for example in the applications WO 92/03462, WO 93/16092, WO 93/16091, WO 94/03465, PCT/EP94/02123; DE 4402492, DE 4418690 as well as for example in WO 91/19726, EP 0 350 287, U.S. Pat. Nos. 5,223,263, 5,194,654, 4,921,951, 4,622,392, 4,291,024, 4,283,394. In the case of antivirally active nucleoside derivatives EP 0 350 287 and U.S. Pat. No. 5,223,263 describe lipid derivatives (diacylglycerol nucleosides) and their use in a liposomal form.

The active substances which are frequently also hygroscopic, unstable, incompatible with many common auxiliary substances and have a strong tendency to form gels in aqueous media could not be processed to solid, rapidly disintegrating forms of administration even with the aid of a considerable addition of auxiliary substances. When the active substance-auxiliary substance mixtures or the forms of administration which are produced therefrom are introduced into an aqueous release medium a highly viscous gel layer immediately forms in the boundary phase which makes further rapid dissolution impossible. These gel layers only dissolve very slowly similar to a hydrocolloid matrix and thus have an undesired retarding effect.

Although this retarding effect can be partially compensated by dilution with suitable auxiliary substances, it leads to a tablet size which is not appropriate for the dosage due to the high amounts of auxiliary substances that are required and at higher dosages of active substance monolithic forms of administration can no longer be manufactured.

In addition when the formulation is the same, the in vitro dissolution rate depends on the degree of compaction in the form of administration so that an adequate in vitro dissolution rate was not achievable in the case of compressed forms of administration (e.g. tablets) and also in the case of capsule fillings. In addition tablets produced in this manner often have inadequate hardness and excessive abrasion loss so that high losses occur when producing film coated tablets due to breaking of the tablets in the coating pans used.

The conventional production process leads to a further disadvantage. Due to the dispersion of the active substance in the auxiliary substances required for aqueous granulation, the active substance also comes into contact with incompatible auxiliary substances and thus an adequately high stability of the form of administration can often not be achieved. In addition it was found that the homogeneous distribution of the hygroscopic active substance in the form of administration is not always guaranteed because the particles of active substance rapidly agglomerate to form larger units in the moist medium. However, an inhomogeneous distribution of the active substance in the pharmaceutical mixture with other auxiliary substances is problematic since this can result in different amounts of the active substance in the form of administration when it is processed further to individual dose forms such as tablets or capsules. In addition different lot to lot in vitro dissolution rates of the individual forms of administration resulted within the framework of a technical production of larger amounts which exceeded the usual range of variability despite the same composition of the formulation and the same process steps. However, with regard to the required pharmaceutical safety such risks should be excluded as far as possible when developing pharmaceutical preparations.

For the said reasons it was not possible in the usual manner to arrive at a single form of administration in the desired dosage which has an adequately rapid in vitro dissolution rate using the standard galenic methods of mixing, granulation, spray drying, spray solidification or press granulation of the active substance together with auxiliary substances. Moreover the structure of the granulate adversely affects the stability of the active substance i.e. a satisfactory solution cannot be achieved with conventional methods.

SUMMARY OF THE INVENTION

The object of the invention was therefore to develop improved IR forms of administration of active substances or active substance concentrates which form gels in aqueous media.

The object of the invention is achieved by an IR form of administration in which the gel-forming active substances or active substance concentrates are embedded in an envelope which regulates swelling composed of compatible auxiliary substances which inhibit or compensate the gel formation.

DETAILED DESCRIPTION

Figure 1:
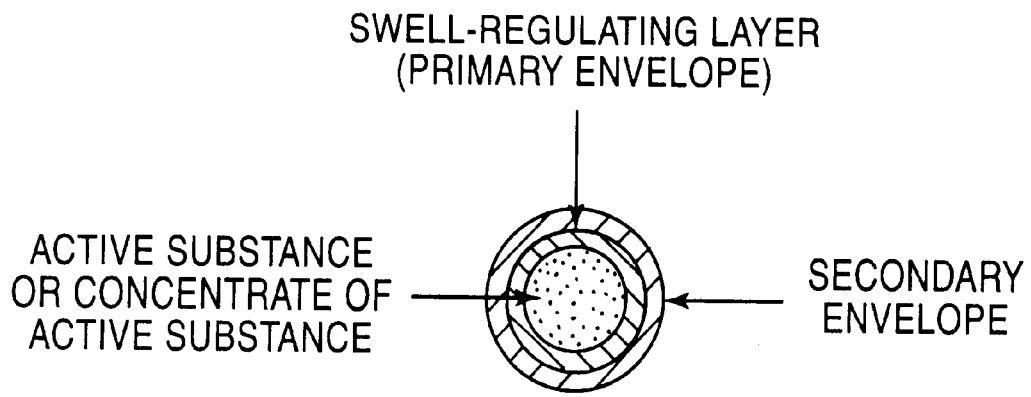
FIG. 1: The inner core of FIG. 1 shows a particle of the active substance with gel forming property, surrounded by a first envelope of auxiliary substances decreasing the gel forming properties and that this envelope additionally is enclosed in a second envelope of other auxiliary substances.

It was surprisingly found that a selected group of auxiliary substances is suitable for reducing or inhibiting or compensating the gel formation of active substances or active substance concentrates in aqueous media within the sense of the invention. Moreover such forms of administration are stable and can be stored for an adequately long period without detectable decomposition products of the active substance or the auxiliary substances used due to possible interactions between the active substance and auxiliary substances. Suitable auxiliary substances within the sense of the invention are macromolecules such as e.g. polyvinyl-pyrrolidones, gelatins, gelatin derivatives, starches, starch derivatives, celluloses, cellulose derivatives, macrogols, polyvinyl alcohols and polyacrylic acids as well as auxiliary substances from the group of sugars, sugar alcohols, glycerides, salts of fatty acids, fats, waxes, surfactants, silicates or highly-dispersed silicon dioxide and combinations thereof. The auxiliary substances highly dispersed silicon dioxide, polyvinyl pyrrolidone, celluloses and sugars come especially into consideration. These auxiliary substances are compatible with the active substances. They can form the swell-regulating envelope either individually or as a combination. The envelope of the active substance particles is in this connection such that each individual active substance particle is surrounded by a primary coat of auxiliary substances and the active substance particles themselves are not in direct contact.

It is well-known that macromolecules (e.g. polyvinyl-pyrrolidones, gelatins, gelatin derivatives, starches, starch derivatives, celluloses, cellulose derivatives, macrogols, polyvinyl alcohols and polyacrylic acids), sugars, sugar alcohols, salts of fatty acids, fats, waxes, surfactants, silicates and also highly-dispersed silicon dioxide can form gels with water or lead to an increase of viscosity in an aqueous medium. Glycerides exhibit comparable effects. Moreover it is known that the aforementioned active substances form gels with aqueous media. Due to these facts it was to be expected that, after the active substance had completely dissolved in aqueous media, an addition of the above-mentioned auxiliary substances would increase the viscosity of the solutions.

However, unexpectedly addition of the said auxiliary substances in the form of a primary coat led to reductions in viscosity i.e. the expected additive effect of active substance and auxiliary substance which should lead to an increase in the viscosity did not occur. It was surprisingly found that the desired rapid in vitro dissolution rates are achieved. In addition the compacted forms of administration (tablets) have the necessary desired physical properties such as adequate hardness and low abrasion loss.

In a preferred embodiment of the invention the active substances or active substance concentrates can also be surrounded by a further envelope (secondary envelope) (see FIG. 1) in addition to the swell-regulating primary envelope.

The same auxiliary substances as for the primary envelope are suitable individually or in combination for the secondary envelope or for embedding the particles provided with a primary envelope.

The solid IR form of administration according to the invention can either be composed of particles with a primary envelope (primary particles), particles with a primary envelope and secondary envelope (secondary particles) or of primary particles (inner phase) with an outer phase or of secondary particles (inner phase) with an outer phase. The outer phase contains those auxiliary substances which are suitable for producing tablets starting with the active substance/auxiliary substance granulates. The outer phase comprises common pharmaceutical auxiliary substances such as fillers and/or agents that aid disintegration and/or flow agents, lubricants or separating agents such as e.g. microcrystalline cellulose, sodium carboxymethyl starch, cross-linked polyvinylpyrrolidone, silicon dioxide or surfactants.

According to the invention the ratio of active substance to auxiliary substance for the IR form of administration is between 1:0.01 and 1:100 for a primary envelope, preferably between 1:0.05 and 1:5. In IR forms of administration with a primary and secondary envelope the weight ratio of active substance to auxiliary substance is in the range of 1:0.01 to 1:10 for the primary envelope and in the range of 1:0.1 to 1:100, preferably 1:1 to 1:10 for the secondary envelope. The content of active substance of the IR form of administration according to the invention is 0.5–90%, preferably 5–50%. The average particle size (d') of the active substance or active substance concentrates in the range of $10\mu$–3 mm. Preferred lower limits are 50 $\mu$m, 100 $\mu$m or 200 $\mu$m. The upper limits are preferably at 500 $\mu$m, 700 $\mu$m or 1 mm.

Gel-forming active substances within the sense of the present invention are in particular understood as those active substances which cause an increase in viscosity of the solution when dissolved in water or in buffer-containing aqueous systems at concentrations of less than 20%, preferably of about 2–10%. The viscosity of such solutions is for example at levels above 5 mPas*sec, in particular of more than 100 mPas*sec and preferably more than 500 mPas*sec.

Active substances or salts or concentrates thereof that form gels in aqueous media according to the invention are for example compounds of the general formula I:

L-B-D     (I)

in which D represents a pharmacologically active substance (drug), L represents a lipophilic residue and B represents a linker group linking the groups L and D.

In particular B denotes a bridge —O—[(PO)(OH)O]$_n$— in which n=1,2,3 and L represents a lipid moiety of the general formula II

(II)

$R^1$—X—$CH_2$
$R^2$—Y—CH
(CH$_2$)$_{\overline{m}}$— in which
  $R^1$ is a straight-chain or branched, saturated or unsaturated alkyl chain with 1–30 carbon atoms which can be optionally substituted once or several times by $C_3$–$C_8$ cycloalkyl or optionally by substituted phenyl groups, halogen, $C_1$–$C_6$ alkoxy, $C_1$–$C_6$ alkyl-mercapto, $C_1$–$C_6$ alkoxycarbonyl, $C_1$–$C_6$ alkylsulfinyl or $C_1$–$C_6$ alkyl-sulfonyl groups $R^2$ is hydrogen, a straight-chain or branched, saturated or unsaturated alkyl chain with 1–20 carbon atoms which can be optionally substituted once or several times by halogen, $C_1$–$C_6$ alkoxy, $C_1$–$C_6$ alkylmercapto, $C_1$–$C_6$ alkoxycarbonyl or $C_1$–$C_6$ alkyl-sulfonyl groups X represents a valency dash, oxygen, sulphur, oxycarbonyl, carbonyloxy, carbonylamido, amidocarbonyl, a sulfinyl or sulfonyl group Y is a valency dash, oxycarbonyl, carbonyloxy, carbonylamido, amidocarbonyl, an oxygen or sulphur atom and m represents an integer between 1 and 5.

$R^1$ in the general formula II preferably denotes a straight-chain or branched $C_8$–$C_{15}$ alkyl group which can additionally be substituted by a $C_1$–$C_6$ alkoxy or a $C_1$–$C_6$ alkylmercapto group. $R^1$ is in particular a saturated alkyl chain which is optionally substituted by a $C_3$–$C_8$ cycloalkyl or an optionally substituted phenyl group. $R^1$ in particular represents a nonyl, decyl, undecyl, dodecyl, tridecyl, tetradecyl, cyclohexyl-hexyl or phenyl-hexyl group in which the phenyl group is optionally substituted by $C_1$–$C_6$ alkyl or halogen. Methoxy, ethoxy, butoxy and hexyloxy groups come into consideration as $C_1$–$C_6$ alkoxy substituents of $R^1$. If $R^1$ is substituted by a $C_1$–$C_6$ alkylmercapto residue, then this is in particular understood as a methylmercapto, ethylmercapto, propylmercapto, butylmercapto and hexylmercapto residue.

$R^2$ preferably denotes a straight-chain or branched $C_8$–$C_{15}$ alkyl group which can additionally be substituted by a $C_1$–$C_6$ alkoxy group or a $C_1$–$C_6$ alkylmercapto group. $R^2$ in particular represents an octyl, nonyl, decyl, undecyl, dodecyl, tridecyl or tetradecyl group. A methoxy, ethoxy, propoxy, butoxy and hexyloxy group preferably come into consideration as $C_1$–$C_6$ alkoxy substituents of $R^2$. $R^2$ denotes in particular a $C_8$–$C_{15}$ alkyl group, preferably an octyl, nonyl, decyl, undecyl, dodecyl, tridecyl and tetradecyl group.

If $R^2$ is substituted by a $C_1$–$C_6$ alkylmercapto residue then this is in particular understood as a methylmercapto, ethylmercapto, butylmercapto and hexylmercapto residue.

X is preferably sulphur, sulfinyl or sulfonyl and Y is oxygen. In special cases the heteroatoms X and Y in the lipid moiety L can be replaced by the carboxylic acid ester known from lecithin since otherwise a hydrolytic cleavage to form the corresponding lysolecithin derivatives or glycerol esters would frequently already occur in the serum or in the liver (first-pass effect) with a corresponding more rapid elimination of the pharmacologically active substance. The thioether lipids and ether lipids (X, Y=O,S) do not exhibit this cleavage in the serum of various species including humans.

Compounds are also preferred in which X and Y represent a valency dash, $R^2$ is hydrogen and $R^1$ represents a $C_1$–$C_{30}$ alkyl chain which can optionally be substituted by $C_1$–$C_6$ alkoxy or $C_1$–$C_6$ alkylmercapto.

m is preferably 1 or 2 and particularly preferably 1.

If the previously-mentioned phenyl groups are substituted, halogen, $C_1$–$C_6$ alkyl, $C_1$–$C_6$ alkoxy, $C_1$–$C_6$ alkylmercapto, $C_1$–$C_6$ alkoxycarbonyl or $C_1$–$C_6$ alkylsulfonyl groups preferably come into consideration as the substituents.

The bridge B is expressed by the formula

—O—[(PO)(OH)O]$_n$— in which n can be 1, 2 or 3 but is preferably 0, 1 or 2 and especially 1.

The lipid moiety L and the phosphate bridge B have the above-mentioned meaning in which L preferably represents a residue of formula II and B is preferably a phosphate bridge. A phosphate bridge is particularly preferred in which n represents 1 and a lipid moiety of formula II is particularly preferred in which $R^1$ and $R^2$ represent an alkyl residue with 8–15 C atoms, X equals sulphur and Y is oxygen.

The term "pharmacologically active substance" (named D in formula I) represents an active substance within the legal pharmaceutical sense. This active substance can be an active substance of a pharmaceutical agent that has already been introduced and licensed by the authorities or an active substance which is currently being registered as a pharmaceutical agent. The definition "pharmacologically active substance" also encompasses such derivatives of active substances that can be chemically modified by introducing one or several functional groups (for example groups which enable D to be coupled to the lipid carrier moiety L such as e.g. hydroxy or amino groups). The definition also encompasses prodrug forms that are formed from the active substance D which are also physiologically active. In particular pharmacologically active substances D come into consideration whose clinical development has been discontinued or not been started due to undesired side effects or which only have a very narrow dose-effect spectrum so that the administration of the therapeutically required amount would be associated with high risks or virtually impossible to get under control.

It is known that the therapeutic range of a pharmacologically active substance is significantly improved when the substance is coupled to a lipid-like carrier molecule. The conjugate prepared in this manner serves as a new active substance for the production of pharmaceutical forms of administration. Overall the coupling results in an increased activity of the pharmaceutically active substance D in vivo since due to the drug-delivery transport system that is formed the pharmacologically active substance is localized in target cells and thus the efficiency of the pharmacologically active substance is increased. This means that on the one hand the amount of pharmacologically active substance that has to be administered can be reduced or on the other hand that an increased pharmacological effect is achieved while retaining the same effective amount.

The chemical structure of the pharmacologically active substances D can in addition be modified in such a way that the substances are changed with regard to their physical or chemical properties and for example have a higher or lower lipophilicity but have essentially the same properties as the unmodified substance D with regard to their therapeutic effect. In particular it is advantageous when the substance D is chemically modified by the introduction of functional groups in such a way that it can be coupled via a suitable bridge to the lipid moiety L. This is for example achieved by the introduction of hydroxy groups which are coupled via the phosphate group B to the lipid. If the active substance already has a phosphate group such as for example in the case of the active substance Foscarnet (HO—P(O)(OH)—COOH), this can also be used directly to couple it to the lipid. In such cases n in the definition of B preferably denotes the number 0.

The pharmacologically active substance D is a chemically or biologically based substance (antibody, peptide, protein, hormone, toxin etc.; INDEX NOMINUM, International Drug Directory, Medpharm) with a biological effect as well as derivatives thereof chemically modified by the introduction of a functional group (e.g. a hydroxy group).

Within the sense of the invention all pharmacologically active substances come into consideration which are effective in vitro but are toxic in vivo in the therapeutic range i.e. all substances with a narrow therapeutic range which have a chemical functional group for a covalent linkage to phosphate. In addition those substances can also be used which, although at first containing no functional groups in their pharmacologically active form, can have one introduced by chemical modification without a loss in the effect of the substance.

Those pharmacologically active substances are preferably used for conjugation with a lipid residue L which normally reach their active form after phosphorylation (such as e.g. in the case of nucleosides). The pharmacologically active substance phosphate is then released from the conjugate by enzymatic hydrolysis of the conjugate. The release of the phosphorylated substance is particularly important since this process can also take place in those cells which do not normally have the necessary enzymes (kinases) to phosphorylate the pure pharmacologically active substance. The conjugated pharmacologically active substance that is released by cleavage by intracellular enzymes can for example have a cytostatic, cytotoxic, antitumoral, antiviral, antiretroviral, immuno-suppressive or immuno-stimulating effect.

If the compounds of formula I contain proton-cleaving residues such as e.g. one or several carboxy, phosphate, or sulfonyl groups, the corresponding esters with alcohols as well as the pharmacologically tolerated salts of these acids such as e.g. alkaline or alkaline earth salts thereof can also be used within the sense of the invention. The corresponding esters are in particular $C_1$–$C_6$ alkyl esters such as e.g. methyl or ethyl esters. Pharmacologically acceptable salts are in particular sodium and potassium salts.

Compounds that are suitable as pharmacologically active substances D which can be optionally converted into a derivative capable of coupling by introduction of a functional group which does not significantly influence its action which then for example slows tumour growth, is a substance which intercalates into DNA and/or RNA, inhibits topoisomerase I and II, is a tubulin inhibitor, is an alkylating agent, is a ribosome inactivating compound, is a tyrosine phosphokinase inhibitor, is a differentiation inducer, a hormone, hormone agonist or hormone antagonist, is a substance which changes pleiotropic resistance to cytostatic agents, is a calmodulin inhibitor, is a protein kinase C inhibitor, is a P-glycoprotein inhibitor, is a modulator of mitochondrially bound hexokinase, is an inhibitor of γ-glutamylcysteine synthetase or glutathione-S transferase, is an inhibitor of superoxide dismutase, is an inhibitor of reverse transcriptase of HIV-1 and HIV-2.

The pharmacologically active substance D can have an antiinflammatory, antirheumatic, antiphlogistic, analgetic or antipyretic action. It can in addition be an antiarrhythmic agent, a calcium antagonist, antihistamine drug, an inhibitor of phosphodiesterase or a sympathomimetic or parasympathomimetic.

All substances are suitable as the pharmacologically active substances D which have a short half-life, in particular also compounds with different organ, tissue or cell half-lives, a poor bioavailability i.e. a poor resorption, high liver cleavage or rapid elimination, poor membrane penetration (e.g. cell membrane, blood-brain barrier), bone-marrow toxicity or other limiting organ toxicities (e.g. cardiotoxicities, liver-toxicities, nephrotoxicities, neurotoxicities etc), whose active concentration in vivo is too low. In addition substances are suitable which interact specifically with the cell nucleus of the target cells and interfere with the molecular process at the DNA or RNA level such as e.g. antisense oligonucleotides, DNA fragments and which can be used for gene therapy.

Pharmacologically active substances D in formula I are for example: AZT (azidothymidine), FLT (fluorothymidine), 5-FU (5-fluorouridine), 6-MPR, fludarabin, cladribin, pentostatin, ara-C, ara-A, ara-G, ara-R Acyclovir, Ganciclovir, Foscarnet, doxorubicin, 4'-epi-doxorubicin, 4'-deoxy-doxorubicin, etoposide, daunomycin, idarubicin, epirubicin, mitoxantron, vincristine, vinblastine, Taxol, colchicine, melphalan, 3'-deoxy-2-fluoro-adenosine, FdA, 5-ethinyluracil-9-β-D-arabino-furanoside, 5-propinyluracil-9-β-D-arabino-furanoside, d4T, ddU, ddI, ddA, d2T, 2'-deoxy-2',2'-difluorocytidine, 5-trifluoromethyl-2'-deoxyuridine, 5-chloro-2',3'-dideoxy-3'-fluorouridine, 3'-deoxy-3'-fluoromyoinositol, neplanocin A, ribavirin, myoinositol, fialuridine, 3TC, Lamivudine, doxifluridine, Tegafur, hypericin, pseudohypericin, Usevir, Famciclovir, Penciclovir, Carvedilol, actinomycin A, bleomycin, daunorubicin, floxuridine, mithramycin, mitomycin C, mitoxanthrone, streptozotocin, vindesin, netilmycin, amikacin, gentamycin, streptomycin, kanamycin A, tobramycin, neomycin B, plicamycin, papamycin, amphotericin B, vancomycin, foscarnet, idoxuridine, trifluridine, vidarabin as well as morphines, prostaglandines, leukotrienes or cyclosporins. Moreover terfenadin, dexamethasone, terbutalin, prednisolone, fenoterol, orciprenaline, salbutamol, isoprenaline, muscarine, bupranolol oxyphenbutazone, oestrogen, salicylic acid, propranotol, ascorbic acid, spongiadiol, diclofenac, isospongiadiol, flufenamic acid, digoxin, 4-methyl-aminophenazone, allopurinol, theophylline, epoprostenol, nifedipine, quinine, reserpine, methotrexate, chloroambucil, spergualine, ibuprofen, indomethacin, sulfasalazine, penicillinamine, chloroquine also come into consideration.

Preferred pharmacologically active substances are for example also peptides, proteins and oligonucleotides such as e.g. corticotropin, calcitonin, desmopressin, gonadotropin, goserelin, insulin, zypressin, beta-melanotropin, alpha-melanotropin, muramyldipeptide, oxytocin, vasopressin, FK-506, octreotide or enalkiren.

Within the scope of the invention lipid conjugates of nucleosides are preferred active substances. In this connection azidothymidine conjugates, fluorothymidine conjugates and 5-fluorouridine conjugates are particularly preferred. The sodium salt of 3'-azido-3'-deoxy-5'-thymidylic acid-mono[3-(dodecylthio)-2-decyloxy-propyl]-ester, the sodium salt of 3'-fluoro-3'-deoxy-5'-thymidylic acid-mono[3-(dodecylthio)-2-decyloxy-propyl]-ester and the sodium salt of 5-fluoro-5'-uridylic acid-mono [3-(dodecylthio)-2-decyloxypropyl]-ester are particularly preferred. A further preferred lipid conjugate is (3-dodecylmercapto-2-decyloxy)-propoxy-phosphinylhydroxy-formic acid as well as sodium salts and alkyl esters thereof.

The pharmacologically active substances mentioned above and the conjugates which can be produced therefrom only represent examples and do not limit the inventive idea.

The content of the gel-forming active substances per individual form of administration, e.g. in a tablet, is 1–500 mg, preferably 10–300 mg, in particular about 100–250 mg, whereby the weight of the individual form of administration should not exceed 1000 mg. If the individual forms of administration are tablets these can be provided with film-forming coatings in order for example to achieve a taste-regulating effect or an effect which influences the release of the active substance.

The process for the production of the IR forms of administration according to the invention is carried out by the following methods:

1) The swell-regulating primary envelope is applied by mixing, granulation (all variants of build-up or break-down granulation), preferably wet or spray granulation, dry granulation, spray drying, spray solidification or press granulation of the active substance or concentrate of active substance with the aforementioned compatible auxiliary substances either individually or with a combination of these auxiliary substances.

The ratio between active substance and auxiliary substance is between 1:0.01 and 1:100 preferably between 1:0.05 and 1:5 in this process.

2) The application of a secondary envelope is carried out by mixing, granulation (all variants of build-up or break-down granulation), preferably wet or spray granulation, dry granulation, spray drying, spray solidification or press granulation of the primary particles produced according to 1) with the said auxiliary substances either individually or with a combination thereof.

The ratio between the active substance and auxiliary substance is between 1:0.1 and 1:100 preferably between 1:1 and 1:10 in this process.

Optionally the primary particles or secondary particles are admixed in the usual manner with an external phase composed of common pharmaceutical auxiliary substances such as fillers and/or agents aiding disintegration and/or flow agents, lubricants or separating agents.

The IR form of administration according to the invention has an advantageous active substance release of more than 35% after 30 minutes or more than 70% after one hour. The active substance release is preferably at least 80–95% after one hour in particular at least 90%.

The IR form of administration according to the invention with a primary envelope around the active substance particles has the following advantages:

1) Prevention or reduction of gel formation of the active substance particles when they dissolve in an aqueous medium and thus improvement of the in vitro dissolution rate in the final form of administration. p1 2) Avoidance of agglutination of the active substance particles during processing in a moist medium (granulate production) and in the later dissolution of the form of administration in an aqueous medium.
3) Protective function towards active substance-decomposing auxiliary substances in an optional secondary envelope.
4) Shielding the active substance from moisture during the production process and during storage of the form of administration.
5) Increase of the resulting hardness of the compacted material by an improved interlocking of the active substance with other auxiliary substances.

In addition the secondary envelope (or embedding of the active substance particles provided with a primary envelope) has the following additional advantages for the IR form of administration:

1. Significant improvement of the disintegration of the compacted material in the enveloped primary particles (inner phase). As a result the surface is firstly enlarged before the active substance particles provided with a primary envelope start to form a gel.
2. Further physical protection against auxiliary substances in an outer phase which decompose the active substance.
3. Ensures the effectiveness of the external phase (e.g. disintegrant effect).
4. Ability to interlock the individual enveloped particles during tabletting.
5. Masking of the plastic properties of the active substance in order to ensure a perfect compression independent of the compression force resulting in a high hardness and low abrasion loss of the compacted materials.

The preferred process according to the invention for the production of IR forms of administration is that a primary envelope which inhibits gel formation of the active substance is applied in a first step to the active substance surface using the auxiliary substances according to the invention. This is preferably carried out by mixing, granulation, spray drying, spray solidification or press granulation of the active substance with the macromolecular auxiliary substances and optionally with further pharmaceutical auxiliary substances. The active substance particles used preferably have a diameter of 10–500 μm. The particles which are formed in this step then have a diameter of more than 10 μm in particular 50–700 μm. Then in a second step a secondary coating or embedding of the particles obtained in the first step is carried out using the auxiliary substances according to the invention or further pharmaceutical additives. This process step can likewise be carried out by mixing, granulation, spray drying, spray solidification or press granulation of the particles optionally using further granulation additives. The particles obtained in this manner have a two layer structure in which the particle core is formed by the active substance itself, the inner envelope (primary envelope) is composed of a layer or envelope of auxiliary substances which contain the auxiliary substances according to the invention. The other auxiliary substances are then contained in a second envelope (secondary envelope) which is applied to the primary envelope. The ratio of active substance to auxiliary substance is preferably in the range of 1:0.01 to 1:10 in the case of the primary envelope. The ratio of active substance to auxiliary substance in the secondary envelope is preferably 1:0.1 to 1:100. In a third process step the outer phase (e.g. tabletting aid) can then be admixed with the secondary particles so that the tabletting mass produced in this manner can be directly pressed into tablets. The tablets produced in this manner can optionally be coated with a neutral film or with a film that regulates the taste or release of the active substance.

Subsequently it is intended to further elucidate the invention by the following examples without limiting it thereto.

EXAMPLE 1

The variants A and B show conventionally produced forms of administration, variant C is a form of administration according to the invention:

| Pos. | Variants: | A | B | C |
|------|-----------|-----|-----|-----|
| 1) | active substance | 206 mg | 206 mg | 206 mg |
| 2) | silicon dioxide, highly disp. | — | — | 14 mg |
| 3) | microcrystalline cellulose | 142 mg | — | — |
| 4) | lactose | 300 mg | 442 mg | 300 mg |
| 5) | Polyvidon K25 | 4 mg | 4 mg | 20 mg |
| 6) | microcrystalline cellulose | — | — | 176 mg |
| 7) | sodium carboxymethylstarch | 120 mg | 120 mg | — |
| 8) | poly(vinylpyrrolidone),cross-linked | — | — | 40 mg |
| 9) | silicon dioxide, highly disp. | 8 mg | 8 mg | 4 mg |

-continued

| Pos. | Variants: | A | B | C |
|------|-----------|-----|-----|-----|
| 10) | magnesium stearate | 20 mg | 20 mg | 20 mg |
|  | final weight of core | 800 mg | 800 mg | 780 mg |
|  | hardness | 40 N | 28 N | 142 N |
|  | abrasion loss | capping | capping | 0.1% | active substance:

Na salt of 3'-azido-3'-deoxy-5'-thymidylic acid-mono[3-(dodecyl-thio)-2-decyloxypropyl]-ester Gel-forming properties of the active substance: When an aqueous 7% solution of the active substance is prepared the viscosity of the solution is 500–600 mpa*sec (initial value: 1 mPa*sec).

The primary coat is produced in a first step by coating the active substance particle 1) with an aqueous suspension of the auxiliary substance 2) In a second step the secondary coat is prepared by wet granulation of the particles obtained from the first step together with the positions 3)–5). The outer phase is prepared by admixing positions 6)–10). Subsequently the pharmaceutical masses obtained in this manner are tabletted and the hardness and the abrasion loss of the tablets obtained are determined. In variants A and B the production of a primary envelope is omitted.

The example shows that the IR form of administration according to the invention with a primary and secondary coating of the active substance does not cap and exhibits a very low abrasion loss and moreover it has a significantly increased hardness. In variants A and B the gel-forming active substance is processed conventionally to form a granulate with large amounts of disintegration-promoting auxiliary substances (microcrystalline cellulose and lactose) and with the binding agent PVP (Polyvidon K25). In variant 3 the amount of disintegration-promoting auxiliary substances is reduced by ca. one third but the auxiliary substance aerosil (highly dispersed silicon dioxide) is present. Furthermore the coating process used ensures that the active substance particles are surrounded by a continuous coat (primary coat). Tablets with good physical properties are only obtained in variant C whose release fulfils the desired requirements. During the tabletting the capping of the tablets could be reduced to a low value below 1%. In addition the IR form of administration according to the invention already exhibits a 90% release of the active substance after one hour.

EXAMPLE 2

The following three variant forms of administration are prepared analogously to example 1: The variants A and B show conventionally produced forms of administration, variant C is a form of administration according to the invention:

| Pos. | Variants: | A | B | C |
|------|-----------|-----|-----|-----|
| 1) | active substance | 100 mg | 100 mg | 100 mg |
| 2) | silicon dioxide, highly disp. | — | — | 13 mg |
| 3) | Microcrystalline cellulose | 116 mg | — | — |
| 4) | lactose | 200 mg | 316 mg | 200 mg |
| 5) | Polyvidon K25 | 4 mg | 4 mg | 20 mg |
| 6) | microcrystalline cellulose | — | — | 120 mg |
| 7) | sodium carboxymethylstarch | 60 mg | 60 mg | — |
| 8) | poly(vinylpyrrolidone),cross-linked | — | — | 30 mg |
| 9) | silicon dioxide, highly disp. | 5 mg | 5 mg | 2 mg |
| 10) | magnesium stearate | 15 mg | 15 mg | 15 mg |
|  | final weight of core | 500 mg | 500 mg | 500 mg |
|  | hardness | 45 N | 17 N | 150 N |
|  | abrasion loss | capping | capping | <1% | active substance:

R,S-(3-dodecylmercapto-2-decyloxy)-propoxy-phosphinylformic acid (di-sodium salt or methyl ester)

The example shows that there is no capping with the IR forms of administration according to the invention with a primary and secondary envelope around the active substance and they have an extremely low abrasion loss, moreover, they are considerably harder. In addition the IR form of administration according to the invention already has a 80% release of the active substance after one hour.

EXAMPLE 3

The following forms of administration are prepared analogously to example 1, wherein variants A and B concern conventionally produced forms of administration and variant C is a form of administration according to the invention:

| Pos. | Variants: | A | B | C |
|------|-----------|-----|-----|-----|
| 1) | active substance | 150 mg | 150 mg | 150 mg |
| 2) | silicon dioxide, highly disp. | — | — | 10 mg |
| 3) | microcrystalline cellulose | 136 mg | — | — |
| 4) | lactose | 203 mg | 336 mg | 218 mg |
| 5) | Polyvidon K25 | 3 mg | 3 mg | 15 mg |
| 6) | microcrystalline cellulose | — | — | 129 mg |
| 7) | sodium carboxymethylstarch | 87 mg | 90 mg | — |
| 8) | poly(vinylpyrrolidone),cross-linked | — | — | 30 mg |
| 9) | silicon dioxide, highly disp. | 6 mg | 6 mg | 3 mg |
| 10) | magnesium stearate | 15 mg | 15 mg | 15 mg |
|  | final weight of core | 600 mg | 600 mg | 570 mg |
|  | hardness | 33 N | 15 N | 160 N |
|  | abrasion loss | capping | capping | <0.5% | active substance:

Na salt of 3'-fluoro-3'-deoxy-5'-thymidylic acid-mono[3-(dodecyl-thio)-2-decyloxypropyl]-ester Viscosity of a 2% aqueous solution of the active substance: 6 mpas*sec.

The example shows that there is no capping with the IR form of administration according to the invention having a primary and secondary envelope and only slight abrasion and in addition is has a significantly better hardness.

What is claimed is:

1. A solid pharmaceutical preparation, comprising a therapeutically active substance in an envelope, wherein said therapeutically active substance is a compound of formula I

L-B-D (I), wherein L is a lipophilic group of formula II

(II)

wherein
R$^1$ is a straight-chain or branched, saturated or unsaturated C1–C30 alkyl group, and optionally substituted at least once by a halogen atom, a C1–C6 alkoxy or a phenyl;
R$^2$ is a hydrogen or a straight-chain or branched, saturated or unsaturated C1–C20 alkyl, optionally substituted at least once by a halogen atom or a C1–C6 alkoxy; X is an oxygen, sulfur, sulfinyl or sulfonyl group; and
Y is an oxygen, sulfur, sulfinyl or sulfonyl group, wherein
B is a linker group of formula —O—{O(PO)(OH)}$_n$—, wherein n is 0, 1, 2 or 3, and wherein
D is a pharmacologically active substance, wherein the pharmacologically active substance is a therapeutically active nucleoside,
wherein said therapeutically active substance has gel-forming properties in aqueous media, with said active substance being capable of, when dissolved in said aqueous media in a solution at a concentration of less than 20%, increasing the viscosity of said aqueous media to more than 5 mPas.sec; wherein said envelope comprises at least one auxiliary substance capable of reducing the viscosity of an aqueous solution of said active substance; and wherein the pharmaceutical preparation is
(A) in the form of particles having a diameter of more than 10 μm,
(B) capable of releasing, after being in contact with an aqueous media after one hour, more than 70% of said therapeutically active substance, and
(C) suitable for therapy.

2. The pharmaceutical preparation of claim 1, wherein said at least one auxiliary substance is selected from the group consisting of a macromolecule, sugar, sugar alcohol, glyceride, salt of a fatty acid, fat, wax, surfactant and highly dispersed silicon dioxide.

3. The pharmaceutical preparation of claim 2, wherein the macromolecule is selected from the group consisting of polyvinylpyrrolidone, gelatin, starch, cellulose, macrogol, polyvinyl alcohol and polyacrylic acid.

4. The pharmaceutical preparation of claim 1, further comprising a secondary envelope surrounding the primary envelope, wherein the secondary envelope comprises at least one auxiliary substance.

5. The pharmaceutical preparation of claim 4, wherein said at least one auxiliary substance of the secondary envelope is selected from the group consisting of a macromolecule, sugar, sugar alcohol, glyceride, salt of fatty acid, fat, wax, surfactant, silicate and highly dispersed silicon dioxide.

6. The pharmaceutical preparation of claim 5, wherein the macromolecule is selected from the group consisting of polyvinylpyrrolidone, gelatin, starch, cellulose, macrogol, polyvinyl alcohol and polyacrylic acid.

7. The pharmaceutical preparation of claim 1, further comprising an outer phase outside the primary envelope.

8. The pharmaceutically preparation of claim 7, wherein said outer phase is a pharmaceutical auxiliary substance comprising a filler, an agent that aids disintegration, a flow agent, a lubricant or a separating agent.

9. The pharmaceutical preparation of claim 8, wherein said pharmaceutical auxiliary substance is microcrystalline cellulose, sodium carboxymethyl starch, cross-linked polyvinylpyrrolidone, silicon dioxide or a surfactant.

10. The pharmaceutical preparation of claim 4, further comprising an outer phase outside the secondary envelope.

11. The pharmaceutical preparation of claim 10, wherein said outer phase is a pharmaceutical auxiliary substance comprising a filler, an agent that aids disintegration, a flow agent, a lubricant or a separating agent.

12. The pharmaceutical preparation of claim 11, wherein said pharmaceutical auxiliary substance is microcrystalline cellulose, sodium carboxymethyl starch, cross-linked polyvinylpyrrolidone, silicon dioxide or a surfactant.

13. The pharmaceutical preparation of claim 1, wherein the active substance or active substance concentrate and the at least one auxiliary substance are present in a ratio of about 1:0.01 to 1:100.

14. The pharmaceutical preparation of claim 13, wherein said ratio is about 1:0.05 to 1:5.

15. The pharmaceutical preparation of claim 4, wherein the active substance and the auxiliary substances of the primary and secondary envelopes combined are present in a ratio of about 1:0.01 to 1:100.

16. The pharmaceutical preparation of claim 15, wherein said ratio is about 1:0.05 to 1:5.

17. The pharmaceutical preparation of claim 4, wherein the active substance and the at least one auxiliary substance of the primary envelope are present in a ration of about 1:0.01 to 1:10 and the active substance and the at least one auxiliary substance of the secondary envelope are present in a ration of about 1:0.01 to 1:100.

18. The pharmaceutical preparation of claim 17, wherein the active substance or active substance concentrate and the at least one auxiliary substance of the secondary envelope are present in a ratio of about 1:1 to 1:10.

19. The pharmaceutical preparation of claim 1, wherein the content of the active substance is about 0.5 to 90%.

20. The pharmaceutical preparation of claim 19, wherein the content of the active substance is about 5 to 50%.

21. The pharmaceutical preparation of claim 4, wherein the content of the active substance is about 0.5 to 90%.

22. The pharmaceutical preparation of claim 21, wherein the content of the active substance is about 5 to 50%.

23. The pharmaceutical preparation of claim 1, wherein the active substance or active substance concentrate exists as particles having an average particle size of about 0.01 mm to 3 mm.

24. The pharmaceutical preparation of claim 4, wherein the active substance or active substance concentrate exists as particles having an average particle size of about 0.01 mm to 3 mm.

25. The pharmaceutical preparation of claim 1, wherein
R$^1$ is a straight-chain or branched C8–C15 alkyl group, optionally substituted at least once by C3–C8 cycloalkyl or optionally a substituted phenyl;
R$^2$ is a straight-chain or branched C8–C15 alkyl group;
X is sulfur, a sulfinyl or sulfonyl group; and
Y is oxygen,
wherein R$^1$—X— or R$^2$—Y— is a fatty acid ester group at position 1 or 2 of lecithin.

26. The pharmaceutical preparation of claim 25, wherein
R$^1$ is a nonyl, decyl, undecyl, dodecyl, tridecyl, tetradecyl, cyclohexyl-hexyl or phenyl-hexyl group; and $R^2$ is an octyl, nonyl, decyl, undecyl, dodecyl, tridecyl or tetradecyl group, optionally substituted by a $C_1$–$C_6$ alkoxy or $C_1$–$C_6$ alkylmercapto group.

27. The pharmaceutical preparation of claim 26, wherein $R^2$ is an octyl, nonyl, decyl, undecyl, dodecyl, tridecyl or tetradecyl group, optionally substituted by a methoxy, ethoxy, butoxy, hexyloxy, methylmercapto, ethylmercapto, butylmercapto or hexylmercapto group.

28. The pharmaceutical preparation of claim 25, wherein $R^1$ and $R^2$ are independently an alkyl group of 8 to 15 carbon atoms, X is sulfur, Y is oxygen and n is 0 or 1.

29. The pharmaceutical preparation of claim 1, wherein $R^1$ is a $C_1$–$C_{30}$ alkyl group, optionally substituted by a $C_1$–$C_6$ alkoxy or alkylmercapto group, $R_2$ is hydrogen, X and Y are single bonds and m is 1 or 2.

30. The pharmaceutical preparation of claim 1, wherein said therapeutically active substance is a lipid conjugate of a therapeutically active nucleoside.

31. The pharmaceutical preparation of claim 1, wherein said nucleoside is azidothymidine, fluorothymidine, or 5-fluorouridine.

32. The pharmaceutical preparation of claim 1, wherein said therapeutically active substance is capable of, when dissolved in said aqueous media in a solution at a concentration of less than 20%, increasing the viscosity of said aqueous media to more than 100 mPAs.sec.

33. The pharmaceutical preparation of claim 32, wherein said therapeutically active substance is capable of, when dissolved in said aqueous media in a solution at a concentration of less than 20%, increasing the viscosity of said aqueous media to more than 500 mPas.sec.

34. The pharmaceutical preparation of claim 4, wherein said therapeutically active substance is capable of, when dissolved in said aqueous media in a solution of less than 20%, increasing the viscosity of said aqueous media to more than 100 mPas.sec.

35. The pharmaceutical preparation of claim 34, wherein said therapeutically active substance is capable of, when dissolved in said aqueous media in a solution of less than 20%, increasing the viscosity of said aqueous media to more than 500 mPas.sec.

36. A process for making the solid instant-release pharmaceutical preparation of claim 1, comprising mixing, granulating, spray drying or spray solidifying said therapeutically active substance with at least one auxiliary substance to produce particles comprising said active substance coated by said primary envelope, wherein said at least one auxiliary substance inhibits gel formation.

37. The process of claim 36, further comprising mixing, granulating, spray drying or spray solidifying said particles with at least one auxiliary substance to coat said particles coated by said primary envelope with a second envelope.

38. The process of claim 36, wherein said granulating step is wet granulating, spray granulating, dry granulating or press granulating.

39. The process of claim 37, wherein said granulating step is wet granulating, spray granulating, dry granulating or press granulating.

40. The process of claim 36, wherein said at least one auxiliary substance is selected from the group consisting of a macromolecule, sugar, sugar alcohol, glyceride, salt of fatty acid, fat, wax, surfactant, and highly dispersed silicon dioxide.

41. The process of claim 40, wherein the macromolecule is selected from the group consisting of polyvinylpyrrolidone, gelatin, starch, cellulose, macrogol, polyvinyl alcohol and polyacrylic acid.

42. The process of claim 37, wherein said auxiliary substances of the primary and secondary envelopes are independently selected from the group consisting of a macromolecule, sugar, sugar alcohol, glyceride, salt of fatty acid, fat, wax, surfactant, silicate and highly dispersed silicon dioxide.

43. The process of claim 42, wherein the macromolecule is selected from the group consisting of polyvinylpyrrolidone, gelatin, starch, cellulose, macrogol, polyvinyl alcohol and polyacrylic acid.

44. The process of claim 36, further comprising mixing said particles coated with the primary envelope with at least one common pharmaceutical auxiliary substance to enclose said particles with an outer phase.

45. The process of claim 37, further comprising mixing said particles coated with the secondary envelope with at least one common pharmaceutical auxiliary substance to enclose said particles with an outer phase.

46. A method of treating a health disorder treatable with a therapeutically active substance, comprising administering an effective amount of a pharmaceutical preparation of claim 1, containing the therapeutically active substance to a patient in need thereof.

47. A method of treating a health disorder treatable with a therapeutically active substance, comprising administering an effective amount of a pharmaceutical preparation of claim 4 containing the therapeutically active substance to a patient in need thereof.

* * * * *